(12) United States Patent
Chen et al.

(10) Patent No.: US 11,618,727 B2
(45) Date of Patent: Apr. 4, 2023

(54) METHOD FOR PREPARING 3-CHLORO-4-OXOPENTYL ACETATE USING FULLY CONTINUOUS-FLOW MICRO-REACTION SYSTEM

(71) Applicant: Fudan University, Shanghai (CN)

(72) Inventors: Fener Chen, Shanghai (CN); Meifen Jiang, Shanghai (CN); Minjie Liu, Shanghai (CN); Dang Cheng, Shanghai (CN); Chao Yu, Shanghai (CN); Huashan Huang, Shanghai (CN)

(73) Assignee: Fudan University, Shanghai (CN)

( * ) Notice: Subject to any disclaimer, the term of this patent is extended or adjusted under 35 U.S.C. 154(b) by 2 days.

(21) Appl. No.: 17/384,747

(22) Filed: Jul. 24, 2021

(65) Prior Publication Data
US 2021/0355070 A1 Nov. 18, 2021

(30) Foreign Application Priority Data
Feb. 26, 2021 (CN) .......................... 202110212869.2

(51) Int. Cl.
*C07C 67/31* (2006.01)
*B01J 19/00* (2006.01)

(52) U.S. Cl.
CPC ........... *C07C 67/31* (2013.01); *B01J 19/0093* (2013.01); *B01J 2219/00867* (2013.01); *B01J 2219/00894* (2013.01)

(58) Field of Classification Search
CPC .............................. C07C 67/31; B01J 19/0093
See application file for complete search history.

(56) References Cited

FOREIGN PATENT DOCUMENTS

| CN | 107814778 A | 3/2018 |
|---|---|---|
| CN | 111635375 A | 9/2020 |
| CN | 112299995 A | 2/2021 |

OTHER PUBLICATIONS

Liu et al., Synthesis or 3-mercapto-4-oxopentyl acetate, Applied Chemical Industry, vol. 32, No. 6, 2 pages (Year: 2003).*
Wang et al., A proposed mechanism and synthesis of 3-mercapto-4-oxopentyl acetate, Fine chemical Intermediates, vol. 34, No. 5, 2 pages (Year: 2004).*
Daniel Hawksley,a David A. Griffin b and Finian J. Leeper; Synthesis of 3-deazathiamine; Journal of the Chemical Society,Perkin Transactions, 2001, 2, 144.

(Continued)

*Primary Examiner* — Yate' K Cutliff (57) ABSTRACT

This disclosure relates to organic synthesis, and more particularly to a method for preparing 3-chloro-4-oxopentyl acetate using a fully continuous-flow micro-reaction system. In this method, chlorine and an acetylbutyrolactone-containing liquid are simultaneously transported to a first micro-channel reactor for continuous chlorination to obtain α-acetyl-α-chloro-γ-butyrolactone. The reaction mixture is simultaneously transported to a micro-mixer and a second micro-channel reactor together with a mixed solution of glacial acetic acid, hydrochloric acid and water, and the continuous acylation is carried out to obtain 3-chloro-4-oxopentyl acetate. After quenched with a quenching agent, the reaction mixture was subjected to extraction and separation to obtain the 3-chloro-4-oxopentyl acetate.

16 Claims, 1 Drawing Sheet

(56) References Cited

OTHER PUBLICATIONS

Liu Min, Liu Hong, Li Pu-rui; Synthesis of 3-mercapto-4-oxopentyl acetate; Applied Chemical Industry; 2003, 6, 53.

Wang Lieping et al., A Proposed Mechanism and Synthesis Of 3-Mercapto-4-oxopentyl Acetate; Fine Chemical Intermediates; 2004, 5, 34.

Allen A. Thomas et al. Synthesis, in vitro and in vivo activity of thiamine antagonist transketolase inhibitors; Bioorganic & medical chemistry letters, 2008, 6, 2206.

John M. Herbert, Franck Le Strat, Delphine G. Oumeddour, Stephen C. Passey, Keith Taylor, and David M. Whitehead; Synthesis of [thiazolium-2,20-14C2]-SAR97276A from [14C]-thiourea; Journal of Labelled compounds and radiopharmaceuticals, 2011, 2, 89.

Natalia S. Nemeria, et al; Competence of Thiamin Diphosphate-Dependent Enzymes with 2'-Methoxythiamin Diphosphate Derived from Bacimethrin, a Naturally Occurring Thiamin Anti-vitamin; Biochemistry, 2016, 7, 1135.

Lei Zhao et al.; Development of Two Scalable Syntheses of 4-Amino-5-aminomethyl-2-methylpyrimidine: Key Intermediate for Vitamin B1; Organic Process Research&Development; Dev. 2012, 16, 57-60.

Aneurin. Part VII. A Synthesis of Aneurin. By A. R. Todd and F. Bergel. Todd and Bergel: 364-367, 1937.

\* cited by examiner

METHOD FOR PREPARING 3-CHLORO-4-OXOPENTYL ACETATE USING FULLY CONTINUOUS-FLOW MICRO-REACTION SYSTEM

CROSS-REFERENCE TO RELATED APPLICATIONS

This application claims the benefit of priority from Chinese Patent Application No. 202110212869.2, filed on Feb. 26, 2021. The content of the aforementioned application, including any intervening amendments thereto, is incorporated herein by reference in its entirety.

TECHNICAL FIELD

This application relates to organic synthesis, and more particularly to a method for preparing 3-chloro-4-oxopentyl acetate using a fully continuous-flow micro-reaction system.

BACKGROUND 3-chloro-4-oxopentyl acetate of formula (1) is a key fine chemistry intermediate for the synthesis of vitamin Bi, and it also has a wide application in as the fields of medicine, pesticides and dyes.

Several preparation methods of the 3-chloro-4-oxopentyl acetate have been reported. Karaulova, et al. (*Khimya Geterotsiklicheskikh Soedinenii*, 1967, 1, 51) disclosed a method for preparing 3-chloro-4-oxopentyl acetate (1) through reacting α-acetyl-α-chloro-γ-butyrolactone with acetic anhydride in an aqueous acetic acid and hydrochloric acid solution, but the yield of the compound (1) was only 71%. Hawksley, et al. (*Journal of the Chemical Society, Perkin Transactions*, 2001, 2, 144), Plazzi, P. V. et al. (*Farmaco, Edizione Scientifica*, 1981, 11, 921), and Vitali, T. et al. (*Farmaco, Edizione Scientifica*, 1979, 1, 41) all disclosed an other preparation method of 3-chloro-4-oxopentyl acetate (1), in which acetylbutyrolactone (3) and sulfonyl chloride were used as starting materials and reacted to form α-acetyl-α-chloro-γ-butyrolactone (2), and then the compound (2) was reacted with acetic anhydride in the presence of hydrochloric acid to form the compound (1). Unfortunately, the yield of this method was also unsatisfactory (less than 85%). Moreover, Shaps, I. A. et al. (*Khimiko-Farmatsevticheskii*, 1988, 2, 231) disclosed a similar method, in which acetylbutyrolactone (3) was reacted with chlorine to form α-acetyl-α-chloro-γ-butyrolactone (2), and then the α-acetyl-α-chloro-γ-butyrolactone (2) was reacted with acetic acid in the presence of sulfuric acid to form the 3-chloro-4-oxopentyl acetate (1). CoMPared to the previous processes, this method arrived at an elevated yield (86%). On the basis of the above methods, Liu, et al. (*Applied Chemical Industry*, 2003, 6, 53) and Wang, et al. (*Fine Chemical Intermediates*, 2004, 5, 34) both disclosed a method, in which the acetylbutyrolactone (3) was chlorinated with chlorine to form α-acetyl-α-chloro-γ-butyrolactone (2), and then the α-acetyl-α-chloro-γ-butyrolactone (2) underwent a reaction in the aqueous solution of glacial acetic acid and hydrochloric acid under the catalysis of pyridine to obtain the 3-chloro-4-oxopentyl acetate (1). Though this method had a relatively high yield (82-96%), the process was time-consuming (about 4-6 h), and the catalyst pyridine was toxic, which was not conducive to cost saving and green industrial production. Thomas, et al. (*Bioorganic & Medical Chemistry Letters*, 2008, 6, 2206), Herbert, et al. (*Journal of Labelled Compounds and Radiopharmaceuticals*, 2011, 2, 89) and Nemeria, Natalla, S. et al. (*Biochemistry*, 2016, 7, 1135) all disclosed a method, in which acetylbutyrolactone (3) and sulfonyl chloride were reacted to form α-acetyl-α-chloro-γ-butyrolactone (2), which was then reacted with acetic anhydride in an aqueous acetic acid and hydrochloric acid solution under reflux to form the 3-chloro-4-oxopentyl acetate (1). The yield of this method was 89%, however, this method had complicated operation and prolonged reaction process (lasting for several days).

Chinese Patent Publication No. 111635375 proposed a method for preparing 3-chloro-4-oxopentyl acetate (1), in which methyl acetoacetate and propyl 3-bromo-3-chloroacetate were used as starting materials to react with sulfuric acid in a tetrahydrofuran solution containing sodium hydride to form the 3-chloro-4-oxopentyl acetate (1). Although the yield of this method was more than 95%, the method had complicated operation, large time consumption and harsh reaction conditions, and thus it was not conducive to scale-up industrial production.

SUMMARY

This application provides a method for preparing 3-chloro-4-oxopentyl acetate using a fully continuous-flow micro-reaction system to overcome the defects of large time consumption, high safety risk, high energy consumption and low efficiency in the traditional synthesis using a batch reactor. The method provided herein has shortened reaction time, improved yield of the 3-chloro-4-oxopentyl acetate, significantly improved degree of automation and efficiency, greatly reduced energy consumption and greatly enhanced safety, and thus is suitable for industrial production.

This application provides a method for preparing 3-chloro-4-oxopentyl acetate using a fully continuous-flow micro-reaction system, the fully continuous-flow micro-reaction system comprising a first micro-channel reactor, a first micro-mixer, a second micro-channel reactor, a second micro-mixer and an extraction-separation unit communicated in sequence; the extraction-separation unit being composed of at least one extraction separator; and the method comprising:

(1) transporting chlorine and an acetylbutyrolactone-containing liquid simultaneously into the first micro-channel reactor followed by continuous chlorination;

(2) feeding the reaction mixture flowing out of the first micro-channel reactor and a mixed solution of glacial acetic acid, hydrochloric acid and water simultaneously into the first micro-mixer and the second micro-channel reactor in sequence for continuous acylation;

(3) transporting the reaction mixture flowing out of the second micro-channel reactor and an aqueous solution of an inorganic base into the second micro-mixer simultaneously, and transporting the reaction mixture flowing out of the second micro-mixer and an organic solvent to the extraction-separation unit for continuous quenching, extraction and separation; and (4) concentrating the reaction mixture flowing out of the extraction-separation unit under vacuum to obtain a target product 3-chloro-4-oxopentyl acetate;
as shown in the following reaction scheme:

wherein acetylbutyrolactone is shown in formula (3); the 3-chloro-4-oxopentyl acetate is shown in formula (1); and an intermediate α-acetyl-α-chloro-γ-butyrolactone formed from the chlorination is shown in formula (2).

In some embodiments, in step (1), the acetylbutyrolactone-containing liquid is a pure acetylbutyrolactone liquid, or a solution of acetylbutyrolactone dissolved in an organic solvent; the organic solvent is selected from the group consisting of alcohol, ether, ester and ketone; the alcohol is selected from the group consisting of methanol, ethanol, propanol, ethylene glycol, propylene glycol and benzyl alcohol; the ether is selected from the group consisting of isopropyl ether, tetrahydrofuran and 1,4-dioxane; the ester is selected from the group consisting of methyl acetate, ethyl acetate and tert-butyl acetate; and the ketone is selected from the group consisting of acetone, methyl butanone and methyl isobutyl ketone. In an embodiment, the acetylbutyrolactone-containing liquid is the pure acetylbutyrolactone liquid.

In some embodiments, in step (1), the first micro-channel reactor is a tubular micro-channel reactor, a plate-type micro-channel reactor or other commercially available micro-channel reactors.

In some embodiments, in step (1), flows of the chlorine and the acetylbutyrolactone-containing liquid are adjusted such that a molar ratio of the acetylbutyrolactone-containing liquid and the chlorine in the first micro-channel reactor is 1:(0.9-5), preferably 1:(1-3).

In some embodiments, in step (2), a temperature in the first micro-mixer is controlled at −20-50° C., preferably 0-50° C.; and a residence time of the reaction mixture in the second micro-channel reactor is 0.1-30 min, preferably 0.1-10 min.

In some embodiments, in step (2), the first micro-mixer is a static mixer, a T-type micro-mixer, a Y-type micro-mixer, a cross-type micro-mixer, a coaxial flow micro-mixer or a flow-focusing micro-mixer. In an embodiment, the first micro-mixer is the cross-type micro-mixer, the coaxial flow micro-mixer or the flow-focusing micro-mixer.

In some embodiments, in step (2), the temperature in the first micro-mixer is controlled at 0-50° C., preferably 10-30° C.

In some embodiments, in step (2), the second micro-channel reactor is a tubular micro-channel reactor, a plate-type micro-channel reactor or other commercially available micro-channel reactors.

In some embodiments, the tubular micro-channel reactor has an inner diameter of 50 μm-10 mm, preferably 100 μm-5 mm; the plate-type micro-channel reactor comprises a first heat exchange layer, a reaction layer and a second heat exchange layer arranged from top to bottom; wherein the reaction layer is provided with a reaction fluid channel, and a hydraulic diameter of the reaction fluid channel is 50 μm-10 mm, preferably 100 μm-5 mm.

In some embodiments, in step (2), a molar ratio of glacial acetic acid to hydrochloric acid to water in the mixed solution of glacial acetic acid, hydrochloric acid and water is (1-10):(0-5):(0.1-3), preferably (1-5):(0.1-3):(0.1-2).

In some embodiments, in step (2), flows of the reaction mixture flowing out of the first micro-channel reactor and the mixed solution of glacial acetic acid, hydrochloric acid and water are adjusted such that a molar ratio of the intermediate α-acetyl-α-chloro-γ-butyrolactone (2) to acetic acid in the first micro-mixer is 1:(1-10), preferably 1:(2-8).

In some embodiments, in step (2), a temperature in the second micro-channel reactor is controlled at 0-200° C., preferably 50-150° C.; and a residence time of the reaction mixture in the second micro-channel reactor is 1-100 min, preferably 10-80 min.

In some embodiments, in step (3), the second micro-mixer is a static mixer, a T-type micro-mixer, a Y-type micro-mixer, a cross-type micro-mixer, a coaxial flow micro-mixer or a flow-focusing micro-mixer. In an embodiment, the second micro-mixer is the cross-type micro-mixer, the coaxial flow micro-mixer or the flow-focusing micro-mixer.

In some embodiments, in step (3), a temperature in the second micro-mixer is controlled at −10-50° C., preferably 0-30° C.

In some embodiments, in step (3), the at least one extraction separator is each independently a plate-type micro-channel extraction separator, a membrane-type extraction separator, an annulus centrifugal extractor or other commercially available extraction separator. In an embodiment, the plate-type extraction separator has an inner diameter of 100 μm-10 mm and comprises a mixing layer and a separation layer; a membrane of the membrane-type extraction separator is a hydrophobic membrane with a pore size of 0.1-4 μm; the annulus centrifugal extractor has a diameter of 10 cm-1 m; and the extraction-separation unit consists of at least one extraction separator connected in series.

In some embodiments, in step (3), the organic solvent is selected from the group consisting of a halogenated hydrocarbon solvent, an acetate solvent, a substituted benzene solvent and an alkyl ether solvent, preferably the halogenated hydrocarbon solvent or the acetate solvent; the extraction is performed at 10-50° C., preferably 15-35° C.; a residence time of the reaction mixture in each of the at least one extraction separator is 0.1-30 min, preferably 0.1-20 min.

In some embodiments, the fully continuous-flow micro-reaction system further comprises a first feed pump, a gas mass flow controller, a gas-liquid separator, a buffer tank, a first back pressure valve and a second feed pump; the first feed pump is configured to feed the acetylbutyrolactone-containing liquid; one inlet of the first micro-channel reactor is connected to the first feed pump, and the other inlet of the first micro-channel reactor is connected to the gas mass flow controller; an outlet of the first micro-channel reactor is connected to a first port at a top of the gas-liquid separator, a second port at the top of the gas-liquid separator is configured to introduce nitrogen to provide a pressure in the gas-liquid separator; a pressure of the nitrogen is 0.01-2.5 MPa, preferably 0.08-1.5 MPa; a third port at the top of the gas-liquid separator is connected to the first back pressure valve; a back pressure of the first back pressure valve is 0.01-2 MPa, preferably 0.1-1.5 MPa; the pressure of the nitrogen is 0.02-0.5 MPa, preferably 0.1-0.5 MPa, larger than the back pressure set by the first back pressure valve; a liquid outlet of the gas-liquid separator is connected to an inlet of the buffer tank, and an outlet of the buffer tank is connected to the second feed pump.

In some embodiments, the fully continuous-flow micro-reaction system further comprises a third feed pump and a second back pressure valve; the third feed pump is configured to feed the mixed solution of glacial acetic acid, hydrochloric acid and water; one inlet of the first micro-mixer is connected to the third feed pump, and the other inlet of the first micro-mixer is connected to the second feed pump; an outlet of the first micro-mixer is connected to an inlet of the second micro-channel reactor, and an outlet of the second micro-channel reactor is connected to the second back pressure valve; and a back pressure of the second back pressure valve is 0.1-2 MPa, preferably 0.5-1.5 MPa.

In some embodiments, the fully continuous-flow micro-reaction system further comprises a fourth feed pump configured to feed the aqueous solution of the inorganic base and a fifth feed pup configured to feed the organic solvent; one inlet of the second micro-mixer is connected to the fourth feed pump, and the other inlet of the second micro-mixer is connected to an outlet of the second back pressure valve; an outlet of the second micro-mixer is connected to one inlet of the extraction-separation unit, and the other inlet of the extraction-separation unit is connected to the fifth feed pump; one outlet of the extraction-separation unit is connected to a water phase pipeline, and the other outlet of the extraction-separation unit is connected to an organic phase pipeline.

In some embodiments, in step (3), a mass percentage of the inorganic base in the aqueous solution of the inorganic base is 5-50%, preferably 10-45%; and the inorganic base is selected from the group consisting of lithium carbonate, sodium carbonate, potassium carbonate, lithium bicarbonate, sodium bicarbonate, potassium bicarbonate, lithium hydroxide, sodium hydroxide, potassium hydroxide and a combination thereof. In an embodiment, the inorganic base is selected from the group consisting of sodium carbonate, potassium carbonate, sodium bicarbonate, potassium bicarbonate, sodium hydroxide, potassium hydroxide and a combination thereof.

In some embodiments, the step (4) comprises:
collecting an organic phase flowing out of the extraction-separation unit; and
distilling the organic phase to obtain a pale yellow oily product 3-chloro-4-oxopentyl acetate (1).

This application provides a method for preparing 3-chloro-4-oxopentyl acetate using a fully continuous-flow micro-reaction system, which facilitates realizing the scale-up production of the 3-chloro-4-oxopentyl acetate through a multi-channel numbering-up strategy.

Compared to the prior art, this application has the following beneficial effects.

1. The fully continuous-flow micro-channel reaction system has excellent mass transfer, heat transfer and mixing performances, which greatly shortens the reaction time from several days (in the traditional batch reactor) to about 30 min, improves the reaction efficiency and effectively suppresses the side reactions. Compared to the traditional preparation in a batch reactor (yield: about 70%; and purity: about 95%), the method of the disclosure has a significantly improved yield (90%), and the product purity is also increased to 96%.

2. In the method provided herein, the flow of the chlorine can be precisely controlled, which enables the complete quantitative conversion of chlorine in the micro-channel reactor, avoiding the waste of chlorine.

3. This method enables the continuous synthesis of 3-chloro-4-oxopentyl acetate without external intervention, and has advantages of high degree of automation and excellent space-time efficiency, which significantly reduces the labor intensity and production cost.

4. The continuous chlorination of acetylbutyrolactone and chlorine is completed in the reaction fluid channel of the micro-channel reactor, which has a relatively small reaction volume, rendering the online liquid holdup small and the process intrinsically safe.

5. The continuous acylation of α-acetyl-α-chloro-γ-butyrolactone is completed by reacting with a glacial acetic acid solution in the micro-mixer and micro-channel reactor, which avoids the addition of acetic anhydride, thus simplifying the operation and reducing the cost.

6. The multiphase mixing, mass transfer and reaction processes are completed in the micro-mixer and the micro-channel reactor in the absence of a stirring device, which greatly reduces the energy consumption.

7. This method has efficient and simple extraction-separation process, which greatly lowers the time consumption and the equipment cost.

8. The micro-channel reactor facilitates the scale-up production of the 3-chloro-4-oxopentyl acetate through a multi-channel numbering-up strategy.

In the drawings, 1, chlorine gas pipeline; 2, acetylbutyrolactone-containing liquid pipeline; 3, gas mass flow controller; 4, first feed pump; 5, first micro-channel reactor; 6, gas-liquid separator; 7, buffer tank; 8, nitrogen pipeline; 9, first back pressure valve; 10, waste gas treatment device; 11, second feed pump; 12, pipeline of a mixed solution of glacial acetic acid, hydrochloric acid and water; 13, third feed pump; 14, first micro-mixer; 15, second micro-channel reactor; 16, second back pressure valve; 17, pipeline of an aqueous inorganic base solution; 18, fourth feed pump; 19, second micro-mixer; 20, organic solvent pipeline; 21, fifth feed pump; 22, extraction separator; 23, water phase outlet; 24, organic phase outlet; 22-1, mixing layer; 22-2, extraction layer; and 22-3, separation layer.

DETAILED DESCRIPTION OF EMBODIMENTS

In order to render the objects, technical solutions, features and beneficial effects of the disclosure clearer, the disclosure will be described below in detail in conjunction with accompanying drawings and embodiments. It should be understood that these embodiments are merely illustrative of the disclosure, and are not intended to limit the disclosure.

Figure 1:
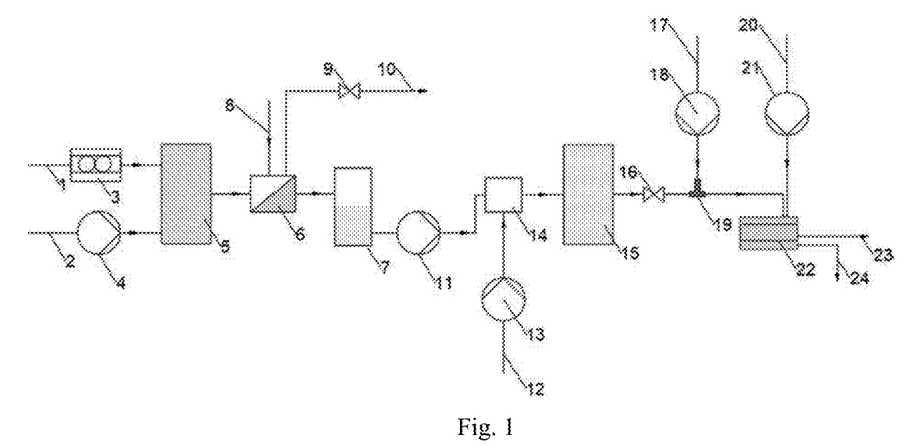
FIG. 1 is a schematic diagram of a micro-reaction system according to an embodiment of the present disclosure.
Figure 2:
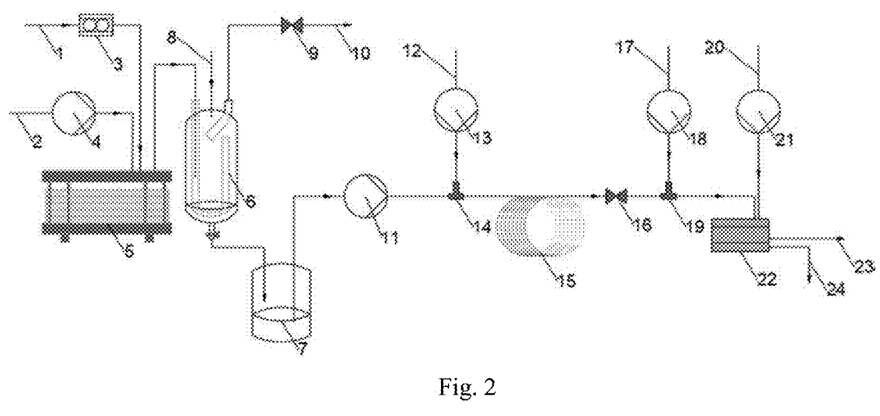
FIG. 2 is a schematic diagram of the micro-reaction system according to an embodiment of the present disclosure.
Figure 3:
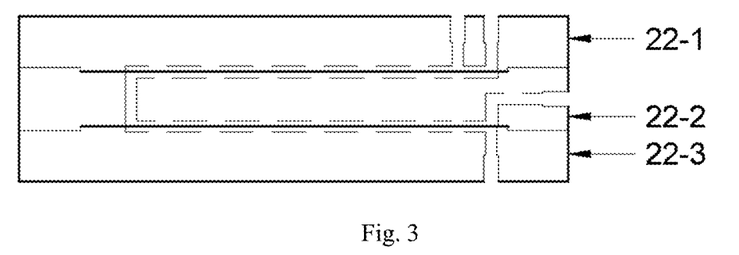
FIG. 3 is a schematic diagram of an extraction separator according to an embodiment of the present disclosure.

A micro-reaction system used in the following embodiments is shown in FIG. 1, which includes a chlorine gas pipeline 1, an acetylbutyrolactone-containing liquid pipeline 2, a gas mass flow controller 3, a first feed pump 4, a first micro-channel reactor 5, a gas-liquid separator 6, a buffer tank 7, a nitrogen pipeline 8, a first back pressure valve 9, a waste gas treatment device 10, a second feed pump 11, a pipeline 12 of a mixed solution of glacial acetic acid, hydrochloric acid and water, a third feed pump 13, a first micro-mixer 14, a second micro-channel reactor 15, a second back pressure valve 16, a pipeline 17 of an aqueous inorganic base solution, a fourth feed pump 18, a second micro-mixer 19, an organic solvent pipeline 20, a fifth feed pump 21 and an extraction separator 22.

One inlet of the first micro-channel reactor 5 is connected to the gas mass flow controller 3, and the other inlet of the first micro-channel reactor 5 is connected to the first feed pump 4. An outlet of the first micro-channel reactor 5 is connected to a first port at a top of the gas-liquid separator 6. A second port at the top of the gas-liquid separator 6 is connected to the nitrogen pipeline 8 to introduce nitrogen, and a third port at the top of the gas-liquid separator 6 is connected to the first back pressure valve 9. A liquid outlet of the gas-liquid separator 6 is connected to an inlet of the buffer tank 7, and an outlet of the buffer tank 7 is connected to one inlet of the first micro-mixer 14 through the second feed pump 11. The other inlet of the first micro-mixer 14 is connected to the third feed pump 13, and an outlet of the first micro-mixer 14 is connected to an inlet of the second micro-channel reactor 15. An outlet of the second micro-channel reactor 15 is connected to the second back pressure valve 16. One inlet of the second micro-mixer 19 is connected to the second back pressure valve 16, and the other inlet of the second micro-mixer 19 is connected to the fourth feed pump 18. An outlet of the second micro-mixer 19 is connected to one inlet of the extraction separator 22, and the other inlet of the extraction separator 22 is connected to the fifth feed pump 21. The extraction separator 22 is provided with a water phase outlet 23 and an organic phase outlet 24 respectively for the discharge of the water phase and the organic phase.

The working process of the micro-reaction system is described as follows.

(A) The acetylbutyrolactone-containing liquid and the chlorine gas are fed to the first micro-channel reactor 5 at the same time respectively through the first feed pump 4 and the gas mass flow controller 3 to carry out continuous chlorination. The reaction mixture flowing out of the first micro-channel reactor 5 enters the gas-liquid separator 6, and the waste gas is discharged through the third port at the top of the gas-liquid separator 6 and the first back pressure valve 9. The reaction mixture is discharged from the outlet at the bottom of the gas-liquid separator 6 and collected into the buffer tank 7.

(B) The reaction mixture in the buffer tank 7 and the mixed solution of glacial acetic acid, hydrochloric acid and water are fed to the first micro-mixer 14 respectively through the second feed pump 11 and the third feed pump 13 and mixed. Then the reaction mixture flows out of the first micro-mixer 14 and directly enters the second micro-channel reactor 15 for continuous acylation reaction.

(C) The reaction mixture flowing out of the second micro-channel reactor 15 is discharged through the second back pressure valve 16 and then enters the second micro-mixer 19. At the same time, the aqueous inorganic base solution is fed to the second micro-mixer 19 through the fourth feed pump 18 and mixed with the reaction mixture. The reaction mixture flowing out of the second micro-mixer 19 directly enters the extraction separator 22 for continuous extraction and separation, where an organic solvent is introduced to the extraction separator 22 through the fifth feed pump 21. An organic phase is discharged from the organic phase outlet 24 of the extraction separator 22, collected and concentrated under vacuum to obtain the target product 3-chloro-4-oxopentyl acetate.

In order to render the objects, technical solutions and beneficial effects of the disclosure clearer, the disclosure will be described below in detail in conjunction with embodiments.

Example 1

An acetylbutyrolactone-containing liquid and chlorine gas were simultaneously transported to a Protrix micro-channel reactor with a reaction volume of 4.3 mL and a micro-channel diameter of 2 mm, where flows of the acetylbutyrolactone-containing liquid and chlorine gas were adjusted such that a molar ratio of the acetylbutyrolactone to chlorine gas was 1:5. A back pressure of a first back pressure valve 9 was set to 0.2 MPa, and a temperature in the Protrix micro-channel reactor was controlled to 25° C. The reaction mixture was reacted in the Protrix micro-channel reactor for 30 s (that was, a residence time of the reaction mixture was 30 s), and then flowed out from an outlet of the Protrix micro-channel reactor. The reaction mixture was separated by a gas-liquid separator 6 to remove gas component, and then collected in a buffer tank 7. The analysis results demonstrated that the substrate acetylbutyrolactone experienced a complete conversion. The reaction mixture in the buffer tank 7 and a mixed solution of glacial acetic acid, hydrochloric acid and water in a molar ratio of 3.5:0:1.5 were transported into a cross-type micro-mixer and mixed, where flows of two feed pumps were adjusted such that a molar ratio of an intermediate α-acetyl-α-chloro-γ-butyrolactone derived from the chlorination to glacial acetic acid was 1:6, and a temperature in the cross-type micro-mixer was controlled to 25° C. The reaction mixture was then transported to a coil-type micro-channel reactor with a length of 10 m and an inner diameter of 0.8 mm to carry out an acylation reaction. A back pressure of a second back pressure valve 16 was set to 2.0 MPa, and a temperature in the coil-type micro-channel reactor was controlled to 140° C. After reacted in the coil-type micro-channel reactor for 30 min (that was, a residence time was 30 min), the reaction mixture was allowed to flow out from the outlet of the coil-type micro-channel reactor, and transported to a T-type micro-mixer together with a saturated sodium bicarbonate solution and mixed to quench the reaction, where a temperature in the T-type micro-mixer was set at 25° C. The reaction mixture was then continuously transported to an extraction separator 22, and ethyl acetate was transported into the extraction separator 22 through another inlet as an extractant. A temperature in the extraction separator 22 was controlled to 25° C. 15 min later (that was, a residence time of the reaction mixture in the extraction separator 22 was 15 min), an organic phase containing the product 3-chloro-4-oxopentyl acetate (1) was discharged from a light phase outlet of the extraction separator 22, and a water phase was discharged from a heavy phase outlet of the extraction separator 22. The organic phase was concentrated under vacuum to produce the target product 3-chloro-4-oxopentyl acetate (1) with a yield of 93% and a purity of 96.7% (GC).

Example 2

The process in this example was basically the same as that of Example 1 except that in this example, the chlorination of acetylbutyrolactone was performed in a tubular micro-channel reactor with a volume of 10 mL and an inner diameter of 1.0 mm; a temperature in the tubular micro-channel reactor was controlled to 50° C.; a back pressure of the first back pressure valve 9 was set to 1.0 MPa; a molar ratio of acetylbutyrolactone (3) to chlorine gas was 1:1.2; the mixing before the acylation reaction was performed in a T-type micro-mixer; a molar ratio of glacial acetic acid to hydrochloric acid to water was 10:0:3; a molar ratio of the intermediate α-acetyl-α-chloro-γ-butyrolactone to glacial acetic acid was 1:4; a temperature in the coil-type micro-channel reactor was controlled to 100° C.; a residence time in the coil-type micro-channel reactor was 80 min; a saturated sodium carbonate solution was used for quenching the reaction; dichloromethane was used as an extractant, and the extraction time was 5 min. In this example, the substrate acetylbutyrolactone experienced a 100% conversion, and the target product 3-chloro-4-oxopentyl acetate (1) had a yield of 89% and a purity of 93% (GC).

Example 3

The process in this example was basically the same as that of Example 1 except that in this example, the chlorination of acetylbutyrolactone was performed in a tubular micro-channel reactor with a volume of 5 mL and an inner diameter of 0.8 mm; a molar ratio of the acetylbutyrolactone (3) to chlorine gas was 1:3; a back pressure of the first back pressure valve 9 was set to 1.0 MPa; a temperature in the tubular micro-channel reactor was controlled to 0° C., and the chlorination was performed for 2 min; a molar ratio of glacial acetic acid to hydrochloric acid to water was 3.5: 0.7:1.5; a molar ratio of the intermediate α-acetyl-α-chloro-γ-butyrolactone to glacial acetic acid was 1:5; a temperature in the cross-type micro-mixer was controlled to 100° C.; a temperature in the coil-type micro-channel reactor was controlled to 200° C.; a residence time in the coil-type micro-channel reactor was 60 min; a back pressure of the second back pressure valve 16 was set to 2.0 MPa; a temperature in the T-type micro-mixer was 0° C.; dichloromethane was used as an extractant (the organic phase flowed out from the heavy phase outlet of the extraction separator 22); a temperature in the extraction separator 22 was controlled to 30° C., and the extraction time was 5 min. In this example, the substrate acetylbutyrolactone experienced a 100% conversion, and the obtained target product 3-chloro-4-oxopentyl acetate (1) had a yield of 90.1% and a purity of 96% (GC).

Example 4

The process in this example was basically the same as that of Example 1 except that in this example, a molar ratio of the acetylbutyrolactone (3) to chlorine gas was 1:0.9; a back pressure of the first back pressure valve 9 was set to 0.5 MPa; and the chlorination was performed for 15 min; a molar ratio of glacial acetic acid to hydrochloric acid to water was 3.5:0.7:1.5, and they were transported to the coaxial flow micro-mixer for mixing; a molar ratio of the intermediate product α-acetyl-α-chloro-γ-butyrolactone to glacial acetic acid was 1:10; a temperature in the coaxial flow micro-mixer was controlled to 25° C.; the second micro-channel reactor 15 for the acylation reaction is the Protrix micro-channel reactor (a volume of 12.6 mL, an inner diameter of 2.0 mm); a back pressure of the second back pressure valve 16 was set to 1.0 MPa; a temperature in the micro-channel reactor 15 was controlled to 125° C.; the reaction time was 15 min; the reaction mixture and saturated solution of potassium bicarbonate were transported to the cross-type micro-mixer together; a temperature in the micro-mixer was controlled to 10° C.; methyl tert-butyl ether was used as an extractant, and a temperature in the extraction separator 22 was controlled to 15° C. In this example, the substrate acetylbutyrolactone was experienced a 100% conversion, and the obtained target product 3-chloro-4-oxopentyl acetate (1) had a yield of 91% and a purity greater than 96% (GC).

Example 5

The process in this example was basically the same as that of Example 1 except that in this example, the methanol solution of acetylbutyrolactone was reacted with chlorine gas, and a temperature in the first micro-channel reactor 5 was controlled to −10° C.; a molar ratio of glacial acetic acid to hydrochloric acid to water was 1:0:0.1; the first micromixer 14 was a flow focusing micro-mixer, and a temperature in the flow focusing micro-mixer was controlled to 50° C.; the acylation reaction was reacted in a plate-type micro-channel reactor (a volume of 5 mL, and an inner diameter of 0.6 mm), a back pressure of the second back pressure valve 16 was set to 0.7 MPa; a temperature in the second micro-channel reactor 15 was controlled to 120° C.; a mixed solution of saturated potassium carbonate and saturated potassium bicarbonate (w:w=50:50) was used for quenching, and dichloromethane was used as an extractant, the extraction separator 22 was a plate-type micro-channel extraction separator, and the reaction mixture was extracted in the extraction separator 22 was 5 min at the room temperature. In this example, the substrate acetylbutyrolactone was experienced a 100% conversion, and the obtained target product 3-chloro-4-oxopentyl acetate (1) had a yield of 90.3% and a purity greater than 96% (GC).

Example 6

The process in this example was basically the same as that of Example 1 except that in this example, the toluene solution of acetylbutyrolactone and chlorine gas were simultaneously transported to the Protrix micro-channel reactor (a volume of 4.3 mL, and a micro-channel diameter of 2 mm); flows of the acetylbutyrolactone-containing liquid and chlorine gas were adjusted such that a molar ratio of the acetylbutyrolactone to chlorine gas was 1:0.9; a temperature in the Protrix micro-channel reactor was controlled to −20° C., and a residence time of the reaction mixture was 5 min; a molar ratio of α-acetyl-α-chloro-γ-butyrolactone derived from the chlorination to glacial acetic acid was 1:1; a static micro-mixer was used herein, and a temperature was controlled to 50° C.; the reaction mixture was transported to the other reaction end of the Protrix micro-channel reactor (a volume of 12.6 mL, and a micro-channel diameter of 2 mm); a back pressure of the second back pressure valve 16 was set to 1.0 MPa; a temperature in the micro-channel reactor was controlled to 135° C., and a residence time of the reaction mixture was 100 min; 20% sodium hydroxide solution was used for quenching; a static micro-mixer was used before extraction, a the temperature in the micro-mixer was 10° C.; a membrane separator was used herein, and chloroform was used as an extractant; a temperature in the membrane separator was controlled to 10° C., and a residence time of the reaction mixture was 30 min. In this example, the obtained target product 3-chloro-4-oxopentyl acetate (1) had a yield of 60.3% and a purity of 90% (GC).

Example 7

The process in this example was basically the same as that of Example 1 except that in this example, the ethanol solution of acetylbutyrolactone and chlorine gas were simultaneously transported to the plate-type micro-channel reactor (a volume of 5 mL, and a micro-channel diameter of 1.0 mm); flows of the acetylbutyrolactone-containing liquid and chlorine gas were adjusted such that a molar ratio of the acetylbutyrolactone to chlorine gas was 1:1.1; a temperature in the plate-type micro-channel reactor was controlled to 30° C., and a residence time of the reaction mixture was 45 s; a molar ratio of glacial acetic acid to hydrochloric acid to water was 5:1:3, and a molar ratio of α-acetyl-α-chloro-γ-butyrolactone derived from the chlorination to glacial acetic acid was 1:1; a coil-type micro-channel reactor used herein had a length of 5 m and an inner diameter of 0.8 mm, a back pressure of the second back pressure valve 16 was set to 2.0 MPa; a temperature in the micro-channel reactor was controlled to 180° C., and a residence time of the reaction mixture was 10 min; 2% potassium carbonate solution was used for quenching; the temperature in the T-type micro-mixer was 20° C.; three annulus centrifugal extractors was used herein, and chloroform was used as an extractant; and a residence time of the reaction mixture was 30 min. In this example, the obtained target product 3-chloro-4-oxopentyl acetate (1) had a yield of 48% and a purity of 90% (GC).

Example 8

The process in this example was basically the same as that of Example 1 except that in this example, a temperature in the micro-channel reactor of the chlorination reaction was controlled to −20° C., and a residence time of the reaction mixture was 10 min; a molar ratio of glacial acetic acid to hydrochloric acid to water was 6.5:1:2.5, and a molar ratio of α-acetyl-α-chloro-γ-butyrolactone derived from the chlorination to glacial acetic acid was 1:5.5; a temperature in the micro-channel reactor of the acylation reaction was controlled to 117° C., and a residence time of the reaction mixture was 55 min; a back pressure of the second back pressure valve 16 was set to 1.5 MPa; a temperature in the extraction separator was 25° C., and a residence time of the reaction mixture was 1 min. In this example, the substrate acetylbutyrolactone was experienced a 100% conversion, and the obtained target product 3-chloro-4-oxopentyl acetate (1) had a yield of 91% and a purity of 95.4% (GC).

Example 9

The process in this example was basically the same as that of Example 1 except that in this example, the extraction separator 22 had a three-layer PTFE plate-type structure, in which a filter membrane with a pore size of 2.5 μm was provided in the micro-channel between the first layer and the second layer to enhance the extraction and mixing effect, and a hydrophobic membrane with a pore size of 0.45 μm was provided in the micro-channel between the second layer and the third layer to separate the water phase and the organic phase; and a residence time of the reaction mixture in the extraction separator 22 was 5 min. In this example, the substrate acetylbutyrolactone also experienced a 100% conversion, and the obtained target product 3-chloro-4-oxopentyl acetate (1) had a yield of 90% and a purity of 96% (GC).

Example 10

The process in this example was basically the same as that of Example 1 except that in this example, a mixed solution of 20% sodium hydroxide, saturated sodium carbonate and saturated sodium bicarbonate in a weight ratio of 10:45:45 was used for the continuous quenching. In this example, the substrate acetylbutyrolactone experienced a 100% conversion, and the obtained target product 3-chloro-4-oxopentyl acetate (1) had a yield of 90% and a purity of 96% (GC).

The above are only preferred embodiments of the present disclosure, and are not intended to limit the scope of the present disclosure. Any changes, modifications and improvements made by those skilled in the art without departing from the spirit of the present disclosure shall fall within the scope of the present disclosure.

What is claimed is:

1. A method for preparing 3-chloro-4-oxopentyl acetate using a fully continuous-flow micro-reaction system, the fully continuous-flow system comprising a first micro-channel reactor, a first micro-mixer, a second micro-channel reactor, a second micro-mixer and an extraction-separation unit communicated in sequence; the extraction-separation unit being composed of at least one extraction separator, and the method comprising:
   (1) transporting chlorine gas and an acetylbutyrolactone-containing liquid simultaneously into the first micro-channel reactor followed by continuous chlorination;
   (2) feeding the reaction mixture flowing out of the first micro-channel reactor and a mixed solution of glacial acetic acid, hydrochloric acid and water simultaneously into the first micro-mixer and the second micro-channel reactor in sequence for continuous acylation;
   (3) transporting the reaction mixture flowing out of the second micro-channel reactor and an aqueous solution of an inorganic base into the second micro-mixer simultaneously, and transporting the reaction mixture flowing out of the second micro-mixer and an organic solvent to the extraction-separation unit for continuous quenching, extraction and separation; and
   (4) concentrating the reaction mixture flowing out of the extraction-separation unit under vacuum to obtain a target product of 3-chloro-4-oxopentyl acetate;
   as shown in the following reaction scheme:

wherein acetylbutyrolactone is shown in formula (3); the 3-chloro-4-oxopentyl acetate is shown in formula (1); and an intermediate α-acetyl-α-chloro-γ-butyrolactone formed from the chlorination is shown in the formula (2).

2. The method of claim 1, wherein in step (1), the acetylbutyrolactone-containing liquid is a pure acetylbutyrolactone liquid, or a solution of acetylbutyrolactone dissolved in an organic solvent; the organic solvent is selected from the group consisting of alcohol, ether, ester and ketone; the alcohol is selected from the group consisting of methanol, ethanol, propanol, ethylene glycol, propylene glycol and benzyl alcohol; the ether is selected from the group consisting of isopropyl ether, tetrahydrofuran and 1,4-dioxane; the ester is selected from the group consisting of methyl acetate, ethyl acetate and tert-butyl acetate; and the ketone is selected from the group consisting of acetone, methyl butanone and methyl isobutyl ketone.

3. The method of claim 1, wherein in step (1), flows of the chlorine and the acetylbutyrolactone-containing liquid are adjusted such that a molar ratio of the acetylbutyrolactone-containing liquid and chlorine in the first micro-channel reactor is 1:0.9-5.

4. The method of claim 1, wherein in step (2), a temperature in the first micro-mixer is controlled at −20-50° C., and a residence time of the reaction mixture in the second micro-channel reactor is 0.1-30 min.

5. The method of claim 1, wherein in step (2), the temperature in the first micro-mixer is controlled at 0-50° C.

6. The method of claim 1, wherein in step (2), a molar ratio of glacial acetic acid to hydrochloric acid to water in the mixed solution of glacial acetic acid, hydrochloric acid and water is 1-10: 0-5:0.1-3.

7. The method of claim 1, wherein in step (2), flows of the reaction mixture flowing out of the first micro-channel reactor and the mixed solution of glacial acetic acid, hydrochloric acid and water are adjusted such that a molar ratio of the intermediate α-acetyl-α-chloro-γ-butyrolactone (2) to acetic acid in the first micro-mixer is 1:1-10.

8. The method of claim 1, wherein in step (2), a temperature in the second micro-channel reactor is controlled at 0-200° C.; and a residence time of the reaction mixture in the second micro-channel reactor is 1-100 min.

9. The method of claim 1, wherein in step (3), the temperature in the second micro-mixer is controlled at −10-50° C.

10. The method of claim 1, wherein in step (3), the organic solvent is selected from the group consisting of a halogenated hydrocarbon solvent, an acetate solvent, a substituted benzene solvent and an alkyl ether solvent; the extraction is performed at 10-50° C.; a residence time of the reaction mixture in each of the at least one extraction separator is 0.1-30 min.

11. The method of claim 1, wherein in step (3), a mass percentage of the inorganic base in the aqueous solution of the inorganic base is 5-50%; and the inorganic base is selected from the group consisting of lithium carbonate, sodium carbonate, potassium carbonate, lithium bicarbonate, sodium bicarbonate, potassium bicarbonate, lithium hydroxide, sodium hydroxide, potassium hydroxide and a combination thereof.

12. The method of claim 1, wherein the first micro-channel reactor and the second micro-channel reactor are independently a tubular micro-channel reactor or a plate-type micro-channel reactor;
the first micro-mixer and the second micro-mixer are independently a static mixer, a T-type micro-mixer, a Y-type micro-mixer, a cross-type micro-mixer, a coaxial flow micro-mixer or a flow-focusing micro-mixer; and
in step (3), the at least one extraction separator is each independently a plate-type micro-channel extraction separator, a membrane-type extraction separator or an annulus centrifugal extraction separator.

13. The method of claim 12, wherein the tubular micro-channel reactor has an inner diameter of 50 μm-10 mm; the plate-type micro-channel reactor comprises a first heat exchange layer, a reaction layer, and a second heat exchange layer arranged from top to bottom; the reaction layer is provided with a reaction fluid channel, and a hydraulic diameter of the reaction fluid channel is 50 μm-10 mm; and
the plate-type extraction separator has an inner diameter of 100 μm-10 mm and comprises a mixing layer and a separation layer; a membrane of the membrane-type extraction separator is a hydrophobic membrane with a pore size of 0.1-4 μm; the annulus centrifugal extractor has a diameter of 10 cm-1 m; and the at least one extraction separator is connected in series to form the extraction-separation unit.

14. The method of claim 13, wherein in step (1), the fully continuous-flow micro-reaction system further comprises a first feed pump, a gas mass flow controller, a gas-liquid separator, a buffer tank, a first back pressure valve and a second feed pump; the first feed pump is configured to feed the acetylbutyrolactone-containing liquid; one inlet of the first micro-channel reactor is connected to the first feed pump, and the other inlet of the first micro-channel reactor is connected to the gas mass flow controller; an outlet of the first micro-channel reactor is connected to a first port at a top of the gas-liquid separator, a second port at the top of the gas-liquid separator is configured to introduce nitrogen to provide a pressure in the gas-liquid separator; a pressure of the nitrogen is 0.01-2.5 MPa; a third port at the top of the gas-liquid separator is connected to the first back pressure valve; a back pressure of the first back pressure valve is 0.01-2 MPa; the pressure of the nitrogen is 0.02-0.5 MPa larger than the back pressure set by the first back pressure valve; a liquid outlet of the gas-liquid separator is connected to an inlet of the buffer tank, and an outlet of the buffer tank is connected to the second feed pump.

15. The method of claim 13, wherein in step (2), the fully continuous-flow micro-reaction system further comprises a third feed pump and a second back pressure valve; the third feed pump is configured to feed the mixed solution of glacial acetic acid, hydrochloric acid and water; one inlet of the first micro-mixer is connected to the third feed pump, and the other inlet of the first micro-mixer is connected to the second feed pump; an outlet of the first micro-mixer is connected to an inlet of the second micro-channel reactor, and an outlet of the second micro-channel reactor is connected to the second back pressure valve; and a back pressure of the second back pressure valve is 0.1-2 MPa.

16. The method of claim 13, wherein in step (3), the fully continuous-flow micro-reaction system further comprises a fourth feed pump configured to feed the aqueous solution of the inorganic base and a fifth feed pump configured to feed the organic solvent; one inlet of the second micro-mixer is connected to the fourth feed pump, and the other inlet of the second micro-mixer is connected to an outlet of the second back pressure valve; an outlet of the second micro-mixer is connected to one inlet of the extraction-separation unit, and the other inlet of the extraction-separation unit is connected to the fifth feed pump; one outlet of the extraction-separation unit is connected to a water phase pipeline, and the other outlet of the extraction-separation unit is connected to an organic phase pipeline.

\* \* \* \* \*